Figure 1:
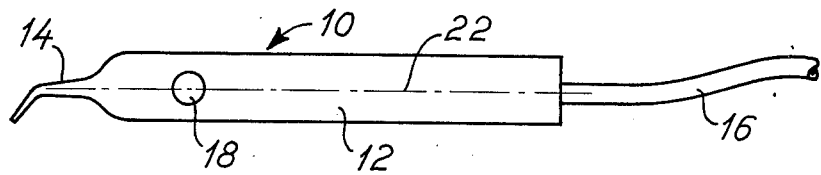

United States Patent [19]
Goof

[11] 4,036,311
[45] July 19, 1977

[54] ROD SHAPED HAND-TOOL

[76] Inventor: Sven Karl Lennart Goof, Gammel Strandvej 236A, Humlebaek, Denmark

[21] Appl. No.: 556,448

[22] Filed: Mar. 7, 1975

[30] Foreign Application Priority Data

Mar. 12, 1974 Denmark .............................. 1334/74

[51] Int. Cl.² .............................................. B23B 45/04
[52] U.S. Cl. ................................ 173/169; 32/DIG. 1; 32/DIG. 3; 32/DIG. 8
[58] Field of Search ................ 251/303; 137/606, 520, 137/521; 173/169; 32/DIG. 1, DIG. 3, DIG. 8, 26, 28

[56] References Cited

U.S. PATENT DOCUMENTS

| | | | |
|---|---|---|---|
| 2,928,174 | 3/1960 | White | 32/DIG. 1 |
| 2,984,452 | 5/1961 | Hooper | 251/303 X |
| 3,032,878 | 5/1962 | White | 32/DIG. 1 |
| 3,048,187 | 8/1962 | Smith | 251/303 X |
| 3,125,809 | 3/1964 | White | 32/DIG. 1 |
| 3,584,832 | 6/1971 | Jackson | 251/303 |
| 3,763,411 | 10/1973 | Goof | 32/DIG. 3 |

Primary Examiner—Ernest R. Purser
Assistant Examiner—Richard E. Favreau
Attorney, Agent, or Firm—Fleit & Jacobson

[57] ABSTRACT

A rod-shaped, manually operable or controllable handpiece is disclosed which e.g., comprises an annular actuating member positioned in a rod-shaped handle portion having actuatable means and a casing for enclosing the actuatable means with which the actuating member is in operative connection. The actuating member comprises at least one ring or disc movable between two positions substantially perpendicularly to the longitudinal axis of the casing, the largest diameter or corresponding external dimensions of said ring or disc being larger than the height or thickness hereof, the axis thereof in said central position being parallel to the longitudinal axis of the casing, and the external side thereof in the central position flushing with or extending equally outside the surface of the casing and whereby the axis of the ring in the outer position is displaced parallel to or forms an acute angle with the axis of the casing. Hereby a considerable reduction of the space necessary for the actuating member in the handle of the handpiece is obtained. It is an additional advantage that the operator obtains equal actuating of the actuating member by equal compressive stress, independently of the location of the stress on the ring.

19 Claims, 12 Drawing Figures

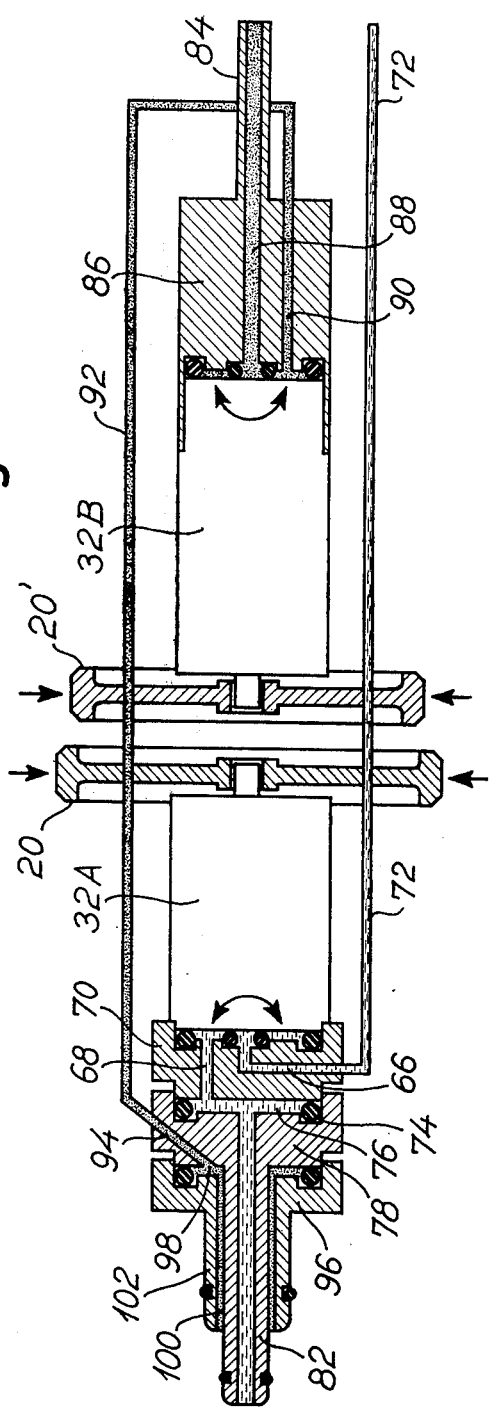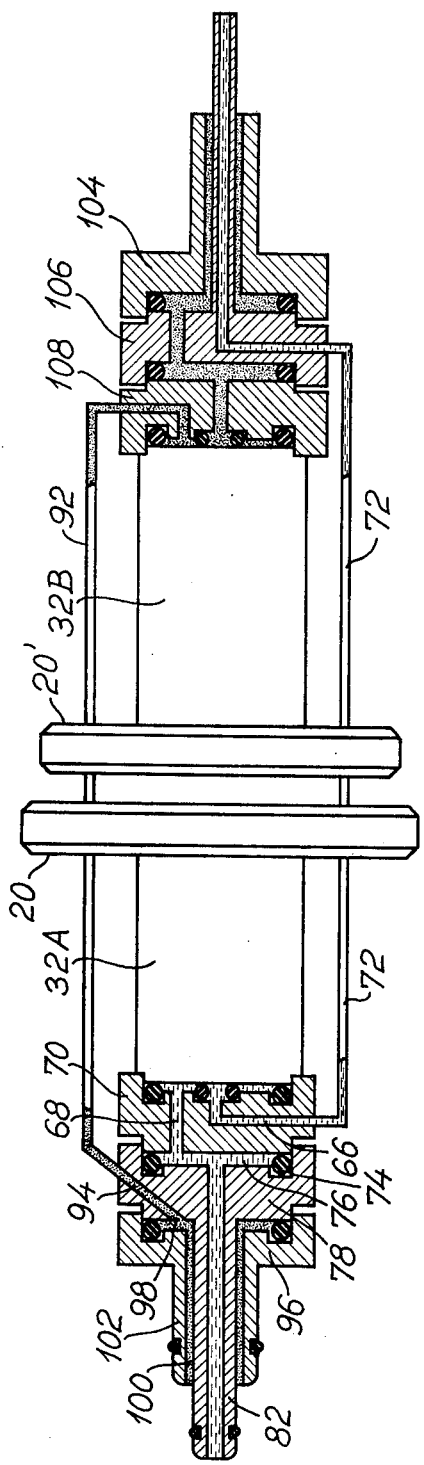

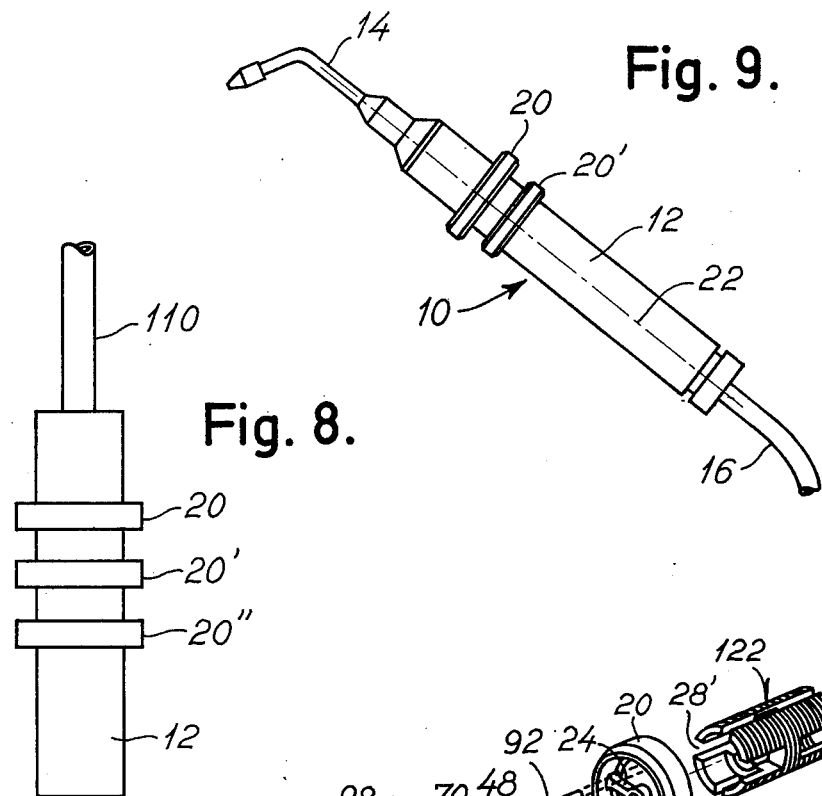
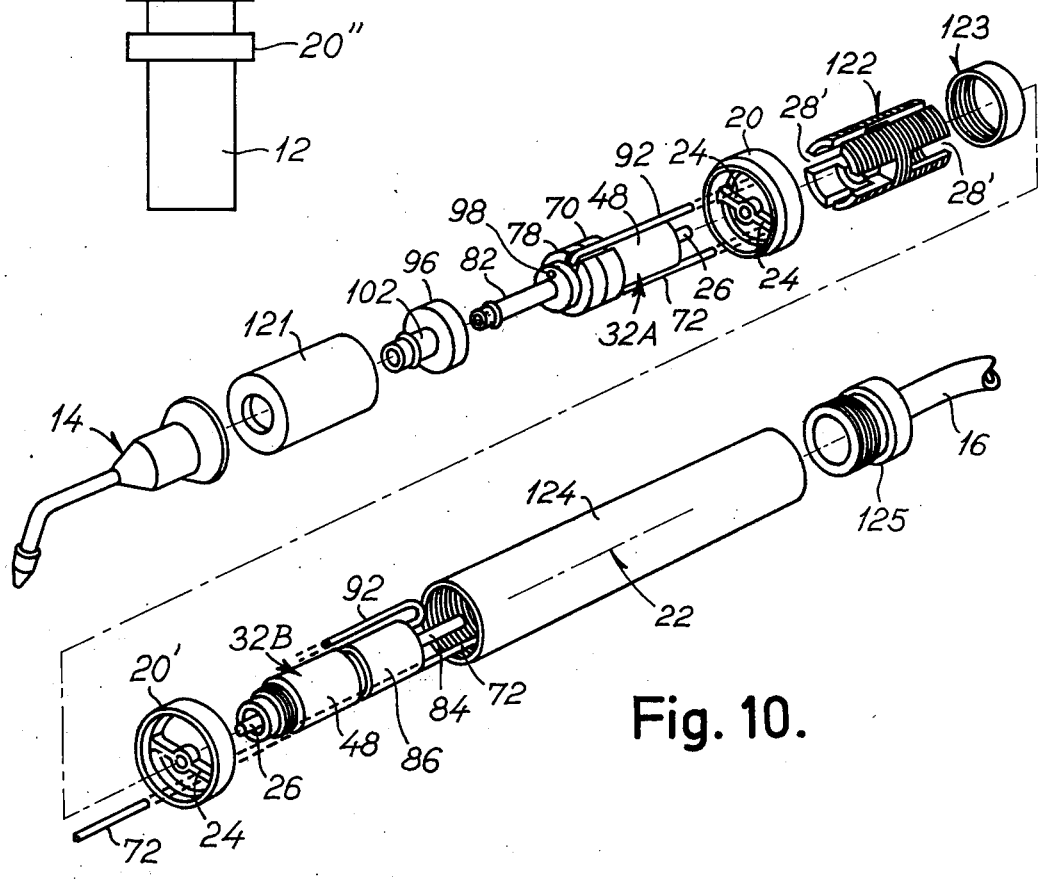

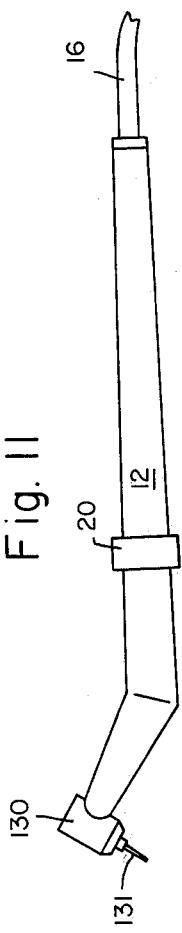
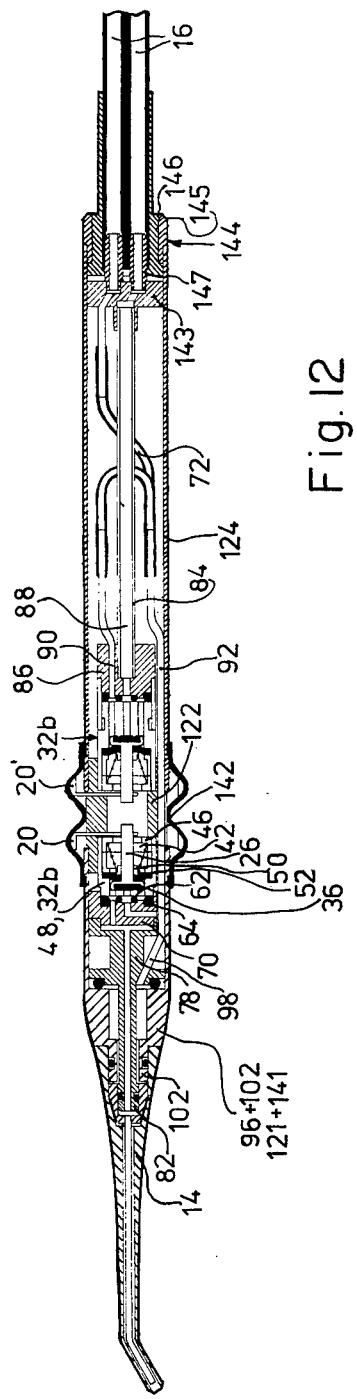
Fig. 11
Fig. 12

ROD SHAPED HAND-TOOL

This invention relates to a rod-shaped handpiece, e.g., a dental syringe, a drilling instrument, a blow gun, a welding gun, a mixing gun, a soldering gun, a remote control handle or the like manually operable or controllable handpieces, said handpiece comprising an annular actuating member positioned in a rod-shaped handle portion having energy supplying means, energy removing means, actuatable means and a casing for enclosing the actuatable means with which the actuating member is in operative connection, said actuating member by a manual press being movable from a central position to an outer position, from which outer position it is moved back to the central position by a return member, e.g., a spring, when the pressure has ceased.

From the prior art, e.g., for crane control, there is known a rod-shaped handpiece provided with several control means which handpiece is suspended in a cable and where each control means is in the shape of a pushbutton operatively connected with a microswitch controlling the energy supply to one of the crane devices. In order to operate the control means the handpiece must be turned round its longitudinal axis after having been gripped until the control means to be influenced faces the thumb of the operator and it is only then the pushbutton in question can be actuated.

From U.S. Pat. No. 3,032,878 a handpiece of this kind is known for dental treatment, said handpiece at one end being connected with a tube or cable for supply of pressurized fluid and at its other end carrying a pneumatic drill to be controlled by a bell-shpaed sleeve in operable connection with a valve for simultaneous control of a cooling medium such as water or air and of the rotatory speed of the drill. In order to obtain a reasonable leverage which is not too difficult to the operator of the handpiece, the actuating member has a longitidinal extension at least of the same size as the diameter of the handle portion.

Another problem is that the operator may actuate the bell-shaped actuating member in a number of places of its longitudinal extension and the manual push which the operator is to exert to start the pneumatic drill of the handpiece, is therefore dependent on the distance of the actuated point from the tilting axis of the lever arm. To avoid this drawback the operator must see to it that the push is exerted on the farthest edge of the actuating member relative to the tilting axis, since, otherwise, he does not get an equal actuation of the actuating member for an equal push. This drawback is partly remedied by means of an adjustable stop-nut for restriction of the tilting movement of the actuating member, but the stop-nut takes up additional space in the handle.

According to a preferred embodiment of the present invention, the actuating member comprises at least one ring or disc movable between said positions substantially perpendicularly to the longitudinal axis of the casing, the largest diameter or corresponding external dimensions of said ring or disc being larger than the height or thickness thereof, the axis thereof in said central position being parallel to the longitudinal axis of the casing, and the external side thereof in the central position flushing with or extending outside the surface of the casing, and the axis of the ring in the outer position is displaced parallel to or forms an acute angle with the axis of the casing.

Hereby an improvement of the rodshaped handpieces hitherto known is obtained, since a considerable reduction of the space necessary for the actuating member at the handle of the handpiece is obtained. Thus, without any constructive difficulties a larger number of actuating members may be provided in the space occupied by a single leverage actuation in the prior art. Furthermore, the possibility of actuating the lever of the actuating members in the handle is still present, since this may take place in the interior of the handle. It is an additional advantage that the operator obtains equal actuating of the actuating member by equal push independently of the location of the push on the ring, which is due to the small extent of the ring or disc.

Each actuating member of the handpiece comprises a ring located around the rod-shaped piece at a suitable spot between its ends. The ring may be elliptic, circular or angular or have the same transverse outline as the rod-shaped piece. Since the ring partly extends round the piece and partly has a small extent in its longitudinal direction, it can be actuated by the operator's fingers in all positions of the piece round its longitudinal axis, and, furthermore, each value of push corresponds to a certain displacement of the ring, and the operator needs therefore only to draw his attention to the direction of the instrument, if it is a handtool, and only to find the correct ring, if it is a control handle for remote control of a machine.

The normal, starting or central position of the ring is the one where the plane of the ring is perpendicular to the longitudinal axis of the casing at the location of the ring on the casing, or in other words where the axis of the ring is parallel to and, possibly, also identical with the longitudinal axis of the casing. The actuated, end or outer position of the ring is the one where the ring cannot be displaced parallelly any farther from its central position or where the axis of the ring in view of mechanical restrictions forms the largest angle possible with the longitudinal axis of the casing near the location of the ring.

The ring is moved from its central to its outer position by a push, e.g., of a finger, anywhere on the ring and as the ring is also operatively connected with a return spring it will be returned to its central position by the spring, when said push has ceased.

The ring may be operatively engaged with a known valve or switch means of the on-off type or the proportional type in the casing. Where it is a question of an on-off type, the ring will close, respectively break a pneumatic, hydraulic, electric or mechanic circuit in its two extreme positions, and where it is a question of the proportional type, the ring, when moved from one position to the other, will change a pneumatic, hydraulic, electric or mechanical circuit from one condition to another condition, and the change of condition is proportional to the distance the ring is moved from its one position toward its other position.

Thus, if the ring is used as an actuating member in, e.g., a dental syringe, it may by its displacing movement cause a change of the valve position for a fulid valve whereby either the fluid flow or the fluid mixture through the handpiece may be changed. A number of devices may be usable for the transmission of the displacing movement of the ring into a change of valve position. In addition, the ring can be adapted to be revolved a circumferential angle.

Hereby it is possible by the same ring manually to control two different functions of the handpiece. E.g., one ring may control two flows of pressurized fluid, where, e.g., the revolving movement of the ring adjusts the ratio of mixture of the pressurized fluids and the diplacing movement controls the rate or quantity of the mixed flow of pressurized fluids through the handpiece, or vice versa.

Where it a question of a rod-shaped handpiece having a number of actuating means according to the invention and where the individual discs or rings serving as actuating means are spaced along the longitudinal axis of the handpiece, it becomes possible for the user of the piece to control even more functions with one hand, if only the rings are positioned within the gripping area of the hand suitably spaced, and here the piece may, e.g., be held between the palm of the operator and at least his little finger, whereby each of the other fingers each may be used to actuate one or two of the actuating rings each having one or two actuating movements.

Where a number of actuating rings is used, one or more thereof may be adapted for actuation by displacement along the longitudinal axis of the handpiece. Like the other rings, this ring may be actuated at any place along the circumference of the rod-shaped handpiece, and in this case it is neither necessary to orient the piece in a definite manner relative to the operator prior to the actuation of the ring.

In a preferred embodiment, the ring may be connected with the actuatable member in the interior of the handle by at least one spoke, and the casing of the handle can for each spoke have an opening larger than the cross section of the spoke.

If the spoke(s) in question are rigidly connected with both the ring and the actuatable member, the displacing movement of the ring must follow a definite path defined by the movement of the actuatbale member, and if this path is circular, the displacing movement of the ring becomes a tilting movement.

If one end of the spokes is rigidly connected with the ring and the other end hinged to the actuatable member, the displacing movement of the ring becomes substantially a parallel displacement perpendicular to the longitudinal axis of the handle.

In a preferred embodiment of a pressurized fluid valve for actuation by the displacing movement of the ring, the valve is provided with a valve rod, one end of which being centrally secured to the actuating ring and the other end of which being secured to a valve body that under spring or fluid pressure is in contact with a valve seat to block its opening, and where the valve body and thereby the valve at the displacement of the ring is tilted about an axis extending in or parallel to the plane of the valve seat mouth. This is obtained by a circular valve body having an annular edge that by the displacement of the ring is brought into contact with an annular collar in the valve seat. This has the effect that a packing centrally positioned in the valve body by leverage is lifted away from the mouth of the valve seat, whereby the pressurized fluid may flow into or out of the mouth. The valve body may also be adapted to block one or two valve seats if the pressurized fluid valve is a mixing valve, whereby the turning movement of the ring e.g. may determine the mixing ratio and the displacing movement of the ring may determine the flow capacity or flow rate.

Instead of a pressurized fluid valve a controllable electric member is as mentioned usable, e.g., a variable resistor, condenser, inductor or the like, and by application of the actuating member for on-off use the valve may be replaced by a switch.

An additional advantage of the embodiment of the handpiece according to the invention, where it is a dental syringe, is that it may be gripped and used with the socalled pengrip. This is not possible by the dental syringes hiterto known which are adapted for pistolgrip. This is of great importance to the dentist that he can grip the syringe by pengrip because this grip is used for his other instruments and apparatuses, e.g., the drill. When all his instruments may be gripped by a pengrip he does not have to waste time for deciding whether the instrument he needs is to be taken by one grip or the other.

The invention will be further described with reference to the accompanying drawing illustrating some preferred embodiments thereof, in which FIG. 1 shows a sketch of the principle of a known rod-shaped handpiece, e.g., a dental syringe, in which the actuating member is a pushbutton, FIG. 2 a sketch of the principle of a dental syringe according to the invention having an actuating member in the shape of an actuating ring, FIG. 3 an enlarged scale sectional view taken on III—III in FIG. 2, FIG. 4 the actuating ring of FIG. 2 in an enlarged scale shown in actuated and unactuated position, respectively, FIG. 5 a preferred seat valve particularly, but not solely, suited for actuation by the actuating ring and shown in an enlarged scale axial view, FIG. 6 schematically and partly in section an embodiment of a rod-shaped handpiece having two actuating ring and appertaining actuatable seat valves, e.g., of the valve type shown in FIG. 5, FIG. 7 an alternative embodiment of the rear part of the handpiece shown in FIG. 6, FIG. 8 a remote control handle according to the invention having three actuating members and suspended in a remote control cable, FIG. 9 a dental syringe according to the invention having two actuating members, FIG. 10 an exploded view of the dental syringe of FIG. 9, FIG. 11 a turbine driven drill according to the invention, and FIG. 12 is an amended embodiment of the dental syringe according to the invention.

In the drawing, numeral 10 designates a dental syringe. The syringe 10 comprises a rod-shaped casing 12 adapted to be held with one hand, and the syringe receives fluid at its one end through an inlet tube 16 and supplies this fluid through an outlet nozzle 14. FIG. 1 shows a known dental syringe in which the quantity of the fluid supplied is manually controlled by means of a pushbutton 18 which may also have the form of a tilting switch. The pushbutton 18 is operably connected with a valve in the casing 12 controlling the flow of the fluid. In order that the dentist is able to operate the pushbutton 18, the casing 12 must first be turned around its longitudinal axis 22 into such a position that the pushbutton is facing the dentist's thumb or forefinger. Then the dentist turns the outlet nozzle 14, said nozzle being rotatable in the casing 12 about the longitudinal axis of the apparatus, into such a position that the syringe 10 — after being introduced into the patient's mouth — is directed toward the location to be treated.

Figure 2:
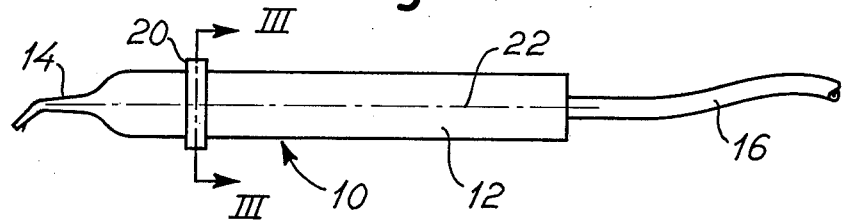

In the embodiment of the present invention shown in FIG. 2, the pushbutton 18 is replaced by a ring-shaped actuating member 20. The syringe shown in FIG. 2 is gripped in the same manner as the known syringe of FIG. 1, but does not have to be oriented in a special way depending on the dentist's thumb or forefinger being placed on the circumference of the casing 12, since the actuating member 20 is adapted to be actuated anywhere on the casing. No matter where the dentist presses the actuating member 20, this has the effect that fluid is supplied from the outlet nozzle 14. Therefore, the outlet nozzle does not have to be rotated into a certain position relative to the position of the actuating member on the casing, before the syringe may be introduced into the patient's mouth, since the dentist can rotate the entire casing in his hand in the patient's mouth simultaneously actuating the actuating member 20 to control the fluid flow through the syringe. The annular actuating member 20 may relative to the casing 12 be displaceably mounted substantially perpendicular to the longitudinal axis 22 of the casing, and the displacement may be a parallel displacement or a tilting movement. The annular actuating member 20 may be an elliptic or a circular ring, or a polygonal ring or a ring the outer surface of which has a circumferential outline following the outer cross outline of the casing near the location of the ring. The ring 20 can have two extreme positions, in one of which its outer surface is in line with or outside the surface of the casing, the axes of the ring and the casing being identical or only parallel, and another extreme position where the axis of the ring either forms an acute angle with the axis 22 of the casing or merely is displaced in parallel on the longitudinal axis 22 of the casing and in a direction substantially perpendicular thereto.

Figure 3:
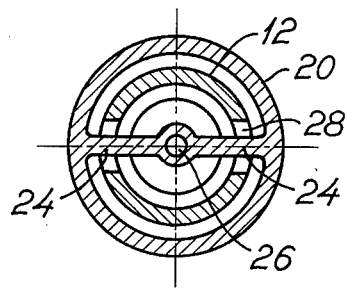

The sectional view of FIG. 3 along the line III—III shows an embodiment for the ring 20. Ring 20 through two rigidly connected spokes 24, is rigidly connected with a valve rod 26 to the valve positioned inside the casing 12. The spokes 24 of the ring extend through openings 28 in the casing 12, which openings 28 are sufficiently large to allow the spokes 24 to be moved unobstructed by the edge of the opening during the tilting or displacement of the ring.

Figure 4:
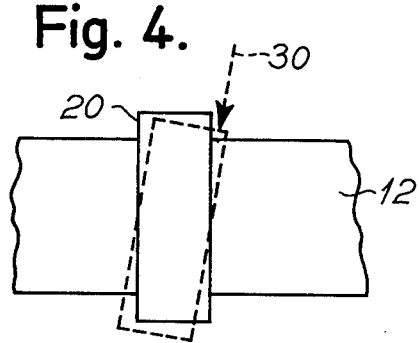

In FIG. 4, the ring 20 shown in FIG. 3 is shown in its normal position and in a position shown in dotted lines, which it assumes when actuated by a certain force of a push 30 resulting from a finger of the hand holding the syringe 10. The fact that the ring 20 makes a tilting movement to come from its normal position to its actuated position is due to the fact that the ring as shown in FIG. 3 is rigidly connected with the valve rod 26, and this valve rod is as shown in FIG. 5 connected with the valve body 34 of the valve 32 in its normal position holding a packing 36 into tight fitting contact with the edge 38 of the valve seat 40. In its actuated position the valve rod 26 at least partly lifts the packing 36 off the edge 38, because the valve body 34 and also the valve rod 26 and the ring 20 tilt about an axis extending through a point of contact between the valve body 34 and the valve seat 40. This point of contact may be situated in a plane through the edge 38 of the valve seat 40 or near this plane and in the embodiment shown in FIG. 5 the point of contact is situated lower than the plane through the edge 38.

Figure 5:
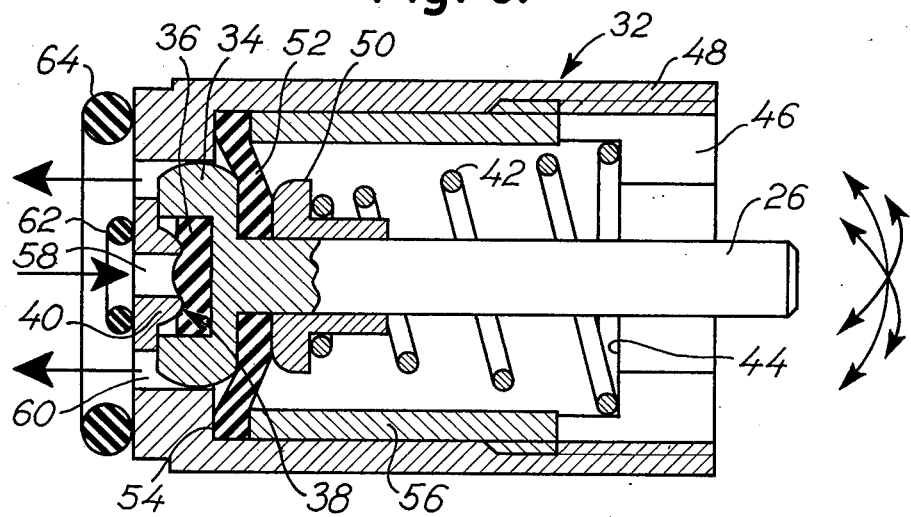

In the embodiment shown in FIG. 5 it is also shown that the valve body 34 in the normal position of the valve abuts a surface on the valve seat 40 and simultaneously the packing 36 is somewhat deformed by the edge 38. Thereby overloading of the packing is avoided. The valve body 34 is kept in its normal position by a valve spring 42 the upper end of which abuts against a collar 44 on a ring 46 screwed into the valve housing 48. The valve spring 42 is conical in the embodiment shown and abuts with its other pointed end against a spring retainer 50 surrounding the valve rod 26. The spring retainer 50 transmits the force of pressure of the spring to the valve body 34 through a sealing diaphragm 52 which is annular and provided with a central hole for the valve rod 26, and which at its outer circular edge abuts tightly against a collar 54 of the valve housing 48 by means of a sleeve 56 pressed in the direction of the collar 54 when the ring 46 is screwed into the valve housing 48. In the normal position of the valve 32 shown in FIG. 5 the valve is in its blocking position, i.e., the connection between passages 60 and the passage 58 discharging into the edge 38 of the valve seat is blocked. When said ring 20, the valve rod 26 and the valve body 34 with its packing 36 are tilted, the connection between the passages 58 and 60 is opened, and when the ring 20 is released, the valve spring 42 will bring the valve and also the ring 20 back to the normal position shown in FIG. 5. No matter where the ring 20 along its circumference is actuated by a force 30 of pressure the result is a tilting of the valve body round a tilting axis the position of which is determined by the point of influence by the force of pressure 30. This valve has proved to be particularly suited for use in dental instruments because it does not squeak as is the case with known valves.

FIG. 5 shows a packing 62 below the valve seat 40 round the passage 58 and a packing 64 below the valve housing round both the passage 58 and the passage 60, and these two packings are used for tight-fitting mounting of the valve 32 in the casing 12 in such a manner as to tightly connect the passges 58 and 60 with appertaining connections in a part of the casing as shown in FIG. 6. In this manner the valve 32A has its passages 58,60 connected to the conduits 66 and 68, respectively in the intermediate cover 70 of the casing 12. Further, FIG. 6 shows two valves 32A and 32B built into the casing 12 and each having control means 20 and 20', respectively which separately or simultaneously can be actuated, e.g., by a finger on the hand gripping the syringe 10. In this embodiment, the syringe 10 is a so-called multi-syringe for two different media, e.g., water and air, and these media can therefore be supplied individually or mixed, depending on the actuation of the rings 20,20'. Water at, e.g., 1-2 atmospheres pressure, is supplied to the valve 32A through a tube 72, the conduit 66 and the passage 58. Depending upon the degree of actuation of the ring 20, water flows through the passages 60 to the passage 68 in the intermediate cover 70. Then, the water flows to an intermediate space 76 sealed by a welded connection or a packing 74 between the intermediate cover 70 and another intermediate cover 78. The water is then conducted in a central conduit and through a tube 82 in the other intermediate cover 78 to a mixing chamber, not shown, in the outlet nozzle 14 of the syringe 10 or to the outermost end of the outlet nozzle 14. Air is also conducted through valve 32B to the mixing chamber, not shown, in the outlet nozzle 14 at, e.g., 3-4 atmospheres pressure and is supplied to the rear end of the casing 12 through a tube 84 in an end cover 86 having a central conduit 88. Conduit 88 is in tight-fitting connection with the passage 58 of the valve 32B from which air, depending on the degree of actuation of the ring 20', is delivered through the passage 60 to a conduit 90 in the end cover 86. Then, the air flows through a tube 92 and is conducted to a conduit 94 in the intermediate cover 78. The air is then conducted to a sealed annular space between the intermediate cover 78 and a front end cover 96 on the casing 12. From the space 98 air is conducted along the exterior of the tube 82 in an annular space 100 between the tube 82 and a tube 102 formed in the end cover 96 for the mixing chamber mentioned above, or to the utmost end of the outlet nozzle 14 where the air meets the liquid from the other valve 32A.

When only the ring 20 is actuated, only water is conducted to the outlet nozzle 14, and when only the ring 20' is actuated, only air is conducted to the outlet nozzle 14 and thereby out through the syringe 10. When both 20 and 20' are actuated, both air and water are conducted to the outlet nozzle 14 and out through the syringe and the mixture proportion and the flow can be adjusted with one single finger abutting both rings 20 and 20'. When the two rings are released, both water and air are cut off. When the syringe 10 is used, the operator only needs to draw his attention to the direction of the outlet nozzle 14 in the patient's mouth and on the degree of actuation of the rings. It is not necessary first to turn the casing 12 round its longitudinal axis 22 to turn the rings in one definite direction and then turn the outlet nozzle 14 to a certain direction before the treatment can take place, and it is neither necessary to remove the syringe from the patient's mouth and then turn the outlet nozzle 14 to a new direction, since this turn can take place with the mouthpiece of the syringe in the patient's mouth. By conducting the water to the outlet nozzle 14 through the tube 82 and the air through the annular space 100, if the water is warmer than the air, it is obtained that the latter can be preheated before the two media mix in the mixing chamber or at the entrance of the outlet nozzle 14. This form of heat exchange can be further improved by supplying the two media as shown in FIG. 7 to the rear end cover of the syringe 10 correspondingly with the water in a central passage and the air in an annular passage positioned round the central passage or vice versa. The two media can also be supplied to the syringe through a twin tube, where one tube is mounted inside the other, whereby also a certain equalization of temperature takes place in the tube itself between the two media.

In FIG. 7 the end cover 86 of FIG. 6 is replaced by three covers 104, 106 and 108, respectively, where the water is supplied through a tube on the end cover 106 to a conduit in said cover, from which the water is conducted to the tube 72 and through this to the valve 32A. The air is supplied to a pipe on the end cover 104 which surrounds the tube on the end cover 106, so that the air flows in the annular clearance between the two tubes to a space between the two end covers 104 and 106. From there the air flows to a conduit in the end cover 106, from where the air flows to a sealed space between the covers 106 and 108 and further through a conduit in the cover 108 to the passage 58 of the valve 32B. Then the air, depending on the actuation of the ring 20', is conducted through the passages 60 of the valve to another conduit in the cover 108, from where the air flows to the tube 92 and forward to the intermediate cover 78 in the other end of the casing 12.

The syringe 10 is in FIG. 9 shown in a preferred embodiment with the two annular actuating members 20,20', respectively, and where the two rings are positioned near one end of the casing 12, so that the syringe can be gripped by a pengrip or in such a manner that the center and the other end of the casing 12 can be used to secure the syringe between at least the little finger and palm in both cases, so that the thumb or forefinger is in a position to actuate the rings separately or simultaneously. It has been found expedient to provide the ring 20 with a greater diameter than the other ring 20'. In general it is, however, preferred that the two rings have the same outer diameter to indicate a change in the ratio of dosage. The width of one ring, e.g., 20' may also be larger than that of the other ring, e.g., 20, whereby a similar effect is obtained. The syringe 10 shown here is also a so-called multi-syringe, because two different media can be supplied from the outlet nozzle 14 separately or mixed in a definite proportion in different controllable amounts. The two media are supplied to the syringe through the inlet tube 16, which in this case consists of two coaxially positioned tubes. The ring 20 or 20' can be of the type shown in FIG. 3 with two rigid connection spokes 24, but the ring may also have one or more than two spokes 24 rigidly connected to the ring. If the ring has at least three spokes, these do not need to be rigidly connected to the ring. For example, if the spokes, instead of being rigidly connected to the valve spindle 26, are hingedly connected with the latter the ring can tilt about a tilting axis in the plane of the ring and still transmit its displacement movement to the valve rod with such a non-rigid connection the ring does not need to tilt relatively to the outside of the casing 12.

Instead of the valve construction shown in FIG. 5, another valve construction can naturally be used, if it only has the quality of being able to change valve position when the ring is moved from its one position to the other. Neither do the valves in the casing 12 need to be closing valves, but one of the valves may, e.g., be a mixing valve for the two media, and the other valve may in that case be a closing valve for the mixed or supplied media.

Instead of valves the casing 12 may contain other actuatable members, such as electrical control means. It is also possible to arrange one or more of the actuatable members in the casing so that rotation of the ring in peripheral direction can be utilized as a controlling movement, whereby each actuating ring 20,20' can be used to adjust two different parameters for the medium flowing through the casing 12.

The annular actuating member 20 is not limited to be used on a dental syringe but may serve as an actuating member for rod-shaped handpieces in general, where a manual operation and/or adjustment of the currents through the hand tool is desired, which currents may be fluid currents or electric currents or energy currents in general. Annular actuating members 20 on such a rod-shaped handpiece may naturally also be used together with other known control devices, such as push- or key buttons, tilting actuators, rotary switches or the like. If, e.g., the rod-shaped handpiece in one end carries a drilling instrument to be controlled by means of an annular actuating member according to the invention, the rotation of the annular actuating member relative to the casing may be used to adjust a lubricant or a coolant for the drill and the object to be drilled, and the tilting movement of the actuating member may serve to control the speed of rotation of the drill.

The annular actuating members according to the invention may also advantageously be used in, e.g., a remote control handle, e.g., for controlling crane operations. Such a handpiece is shown in FIG. 8 of the drawing having, e.g., three annular actuating members 20,20' and 20''. The rod-shaped handpiece shown in FIG. 8 has a casing 12, in which the actuatable members are positioned and connected with the inlet and outlet leads. The inlet and outlet leads, in turn, extend from one end of the handpiece through a control cable 110 in which the handpiece is also suspended. Even if the handpiece is freely rotatable round its axis of rotation it is easy for the operator to grip it and actuate the correct actuating members 20,20' or 20'' according to the invention. The operator does not have to — as in the known remote control handles of this kind — first to turn the handpiece or to move himself, before the actuating members in the form of pushbuttons may be actuated.

A valve operating according to the principle of the pressurized fluid valve mentioned above may also be used elsewhere than in a rod-shaped handpiece. Such a valve may advantageously be used, e.g., as pilot control valve in automatically operating apparatuses or machines whee the valve rod is actuated by a movement from the apparatus or machine. Here, the valve rod may, e.g., be provided with an actuating roller actuated by a steering cam. The valve may also be built into instruments detecting a physical characteristic, e.g., thermostats, level detectors, pressostats etc. where both its property as a proportional and an on-off valve may be utilized. The sensitivity of the valve may be adjusted by means of the spring and the length or rigidity of the valve rod. The valve may also be in the form of a hand valve having large or small dimensions and thereby it has the property that no matter in what direction the operator actuates the valve rod, the valve opens. The valve shown in FIG. 5 might thus receive and control a flow of pressurized gas or fluid through its passages 58, 60, and the valve rod would receive a tilting movement relative to the valve housing 48 and thereby relative to the valve seat 40 by a maneuvering handle or other actuating means.

FIG. 10 shows an exploded view of the instrument shown in FIG. 9. The foremost part of the instrument is the exchangeable outlet nozzle 14 adapted to be coupled to the tube 102 of the end cover 96 and the tube 82 of the intermediate cover 78. These two covers 96 and 78 are connected and inserted in the cap 121 which is the foremost part of the casing 12. The coupling is tight-fitting by means of packings and may be maintained by friction or mechanically by a ball or ratchet lock. Rearward of the intermediate cover 78, with which the tube 92 is connected, there is the intermediate cover 70, with which the tube 72 is connected. The valve 32A has its valve housing 48 tightly connected with the intermediate cover 70 and in the annular actuating member 20 two fixed spokes 24 can be seen. Where the spokes meet, they have a bore as shown in FIG. 3 for attachment at the end of the valve rod 26 of the valve 32A. The end cover 96 and the intermediate covers 70 and 78 and the valve 32A and the ring 20 are secured in the cap 121 when the threaded bush 122 is screwed into the internal thread of the cap 121. Recesses 28' in the threaded bush 122 give a certain margin to the spokes 24 of the ring 20 which is sufficient for the operation of the valve 32A. In the threaded sleeve 122 are external longitudinal recesses for the tubes 72 and 92 and a protective ring 123 is screwed over the threaded bush for protection of its external thread and the tubes 72, 92. The recesses 28' in the threaded bush 122 give also a certain margin to the other ring 20', and the ring 20' is correspondingly attached to the valve rod 26 of the other valve 32B. The valve 32B is tightly fitted in the end cover 86 from which the tube 92 extends forward in the instrument for connection with the intermediate cover 78. From the end cover 86 the centrally positioned tube 84 extends rearwardly with the tube 72, each tube being connected with its inlet conduit in the inlet tube 16 in a way not described in detail. A casing part 124 is threaded in both ends so that at one end it may be screwed into the threaded bush 122 and at its other end may have an end bush 125 screwed thereto. The casing part 124 is adapted to hold the valve 32B and the end cover 86 as well as the tube 84 and the inlet tubes 16 which as mentioned in connection with FIG. 9 consist of two coaxially positioned, flexible inlet tubes for the media in question. The inlet tubes may also be secured to the end cover 86 through a branch connection as shown in FIG. 12 and which is secured to the casing part 124 by means of a thread, a ball lock or the like.

FIG. 11 shows a turbine driven dental drill where the driving medium and the cooling medium are let through the inlet tube 16 at the rear end of the casing 12 and where a turbine 130 in the foremost end of the instrument through a valve in the interior of the casing 12 receives pressurized air at 28-90 psig for rotation of a drill 131 connected with the axis of the turbine 130. The cooling medium, e.g., in the form of cooling water from a separate conduit in the inlet tube 16 is through another valve in the casing 12 channeled to the foremost end of the instrument from which it flows out for cooling the drill and the tooth which is being drilled, and for washing away the material drilled out. The two valves of the casing 12 are in this embodiment of the invention controlled by only one actuating ring 20 which is in operable connection with the actuating rods of both the valves so that when the ring 20 is pressed inwardly from one side, both valves are opened at the same time. However, if the ring is both pressed inwardly and brought to slope only slightly relative to the casing 12, only one valve is opened, whereas the other valve remains closed or opens very little. Thereby it is possible with a single actuating ring in all the positions of the instrument to send substantially only one pressurized medium to the foremost end of the instrument, and thereby drilling may also be performed without supply of liquid or supply of liquid without drilling, if desired.

The actuating ring 20 and the adjacent parts of the surface of the casing 12 may in all embodiments of the invention be surrounded by a tight-fitting mantle of flexible material, e.g., soft PVC, neoprene, etc., so that dust or liquid cannot penetrate into the interior of the casing 12 at the ring 20, at the same time not substantially hindering the movement of the ring 20. For this purpose the mantle may be in the form of a tube having an annular expansion for each actuating ring to be surrounded.

As is the case with the outlet nozzle 14 in the dental syringe mentioned in connection with FIGS. 9 and 10, the foremost end of the dental drill may be easily detachable with a view to replacement or sterilization. Since the packings, e.g., O-rings, are placed in recesses in the foremost end of the casing 12 externally on the tubes 82, 102, respectively, it is easier to sterilize the outlet nozzle 14 or the part holding the turbine, respectively, as these parts have no packings and therefore no internal nuts which would make cleaning difficult. However, they may be provided with external recesses for engagement with a hook or thread on the casing part 12.

FIG. 12 shows a dental syringe in a collected and slightly modified embodiment, as the actuating rings 20 and 20' are covered by a mantle 142. In addition, the outlet nozzle 14 is more streamlined; the end cover 96, the tube 102 and the cap 121 are integrated into a modified end cover 141; the tightening ring between the first interemdiate cover 70 and the second intermediate cover 78 is replaced by a soldered connection; and the end bush 125 is replaced by a branch connection comprisng a fixed part 143 secured in the casing part 124 of the dental syringe and adapted to keep the end cover of the valve 32B in alignment with the tube 84 and the tube conduit 72. Tube 84 and conduit 72 each discharge in a connecting port in the fixed part 143, associating with a movable or detachable part 144 consisting of a union nut 145 which may be screwed into a threaded end of the casing part 124. A tube holder 146 is adapted to hold the tubes 16 and carrying two connecting tubes 147 which are each connected with a tube in the tube holder 146 and each adapted to be tightly fitted in a connecting port in the fixed part 143, when the branch connection is established. Both the tubes 16 and the mantle 142 may advantageously be of silicone rubber.

I claim:

1. A rod-shaped handpiece, such as a dental syringe, a drilling instrument, or the like manually operable or controllable handpieces, the handpiece comprising: a rod-shaped handle portion in the form of a casing having a longitudinal axis; an annular actuating member positioned in said handle portion, having energy supplying means, energy removing means, actuatable means and a casing for enclosing the actuatable means; a return member associating with said actuating member; said actuating member, by a manual press, being movable from a central position to an outer position, from which outer position it is moved back to the central position by said return member when the press has ceased; said actuating member being comprised of at least one ring (20) movable between said positions substantially perpendicularly to said longitudinal axis (22) of the casing, the ring having an axis, a thickness in a direction parallel to its axis, and an external dimension perpendicular to its axis; wherein said external dimension of said ring is larger than the thickness thereof, the axis of said ring, when in said central position, being parallel to said longitudinal axis of the casing, and said external dimension being at least flush with the surface of said casing (12) when said actuating member is in its central position; and wherein the axis of said ring, when in its outer position, is moved relative to the axis of said casing.

2. The handpiece according to claim 1, characterized in that it comprises at least two closely positioned rings (20, 20') each being in operative connection with said actuatable means and that the two rings preferably have the same external dimension.

3. The handpiece according to claim 1, characterized in that it comprises at least two closely positioned rings (20, 20') each being in operative connection with said actuatable means and that of said rings is broader than the other.

4. The handpiece according to claim 1, wherein the external dimension of said ring results in said ring extending outside the surface of said casing.

5. The handpiece according to claim 1 characterized in that the radially outermost surface of the ring (20, 20', 20") has a circumferential outline following the outer cross sectional outline of the casing (12) near to the position of the ring in the casing.

6. The handpiece according to claim 1, characterized in that near to the ring (20) a further ring is provided adapted for displacement relative to the casing.

7. A dental syringe according to claim 1, and further comprising two valve rods (26) and two valves (32A and 32B), for liquid and gas, respectively, preferably water and air, characterized in that it comprises two closely positioned rings (20, 20') each comprising at least one spoke (24) via which the respective rings are associated with said valve rods (26), and that the valves are each fluid-connected with an outlet opening in an outlet nozzle (14).

8. Dental drilling instrument according to claim 1, characterized in that it comprises one ring (20) having at least one spoke (24) which is simultaneously hingedly connected with two valve rods (26) facing each other for valves (32A and 32B) for liquid and gas, respectively, preferably water and air, and that the valve for the gas flow is fluid-connected with a turbine motor (130) of the instrument.

9. The handpiece according to claim 1 characterized in that the ring (20) is connected with said actuatable means in the interior of the casing by at least one connecting spoke (24) and that the casing (12) for each connecting spoke (24) has an opening (28) larger tha the cross section of the connecting spoke.

10. The handpiece according to claim 9, characterized in that it has at least three connecting spokes (24) which at one end are rigidly connected with the ring and at the other end are associated with the actuatable means.

11. The handpiece according to claim 9, characterized in that the connecting spoke (24) is rigidly connected to the ring (20) and to the actuatable means.

12. The handpiece according to claim 1, in which the actuatable means is a fluid valve (32) having a valve rod (26), characterized in that the ring is operably connected with an end of the valve rod (26) of the fluid valve (32), said rod being adapted to open the valve for flow of fluid.

13. The handpiece according to claim 12, characterized in that at the other end of the valve rod, a valve body (34) and a spring (42) are provided, which by means of the pressure of the spring (42) said valve body is brought into contact with a valve seat (40) to block a flow opening thereof, and that the valve body (34) is adapted to open the flow opening of the valve seat when the ring (20), the valve rod (26) and thereby the valve body (34) are tilted about a tilting point in the region of the edge (38) of the flow opening of the valve seat.

14. The handpiece according to claim 12, characterized in that the spring (42) is a conical pressure spring having its smallest windings nearest to the valve body (34).

15. The handpiece according to claim 13, wherein said valve seat has an annular collar and centrally positioned packing, and characterized in that the valve body (34) is circular having an outer edge which during the tilting of the ring (20) and thereby the tilting of the valve rod (26) and the valve body (34), is brought into contact with the annular collar on the valve seat (49) so that action of the valve rod (34) results in the centrally positioned packing (36) being lifted from the edge (38) of the mouth of the valve seat.

16. The handpiece according to claim 1, characterized in that a tight-fitting resilient mantle, preferably of silicone rubber, is provided for encasing said ring and the casing in the immediate vicinity of said ring.

17. The handpiece according to claim 16, characterized in that the mantle is tubular, of uniform thickness and has an annular expansion for each ring (20) and that the internal diameter of the mantle is somewhat smaller than the external diameter of the casing (12) near to the location of the ring (20).

18. A fluid valve comprising a valve housing (48), a valve body (34) having a valve rod (26) integral therewith and supporting a valve packing (36), a valve seat (40) having an orifice (58) normally closed by the packing (36) of the valve body (34), a valve spring (42) forcing the valve body (34) against the valve seat (40) for maintaining the normally closed position, and an abutment shoulder, characterized in that the valve body (34) and the valve rod (26) are mounted to tilt about an arbitrarily directed tilting axis situated in a plane perpendicular to the axis of the valve rod (26) in its normal position, and said plane is parallel to an orifice (58) of the valve seat (40) whereby, when tilting the valve body (34), it abuts said shoulder at a point of said tilting axis and opens the orifice (58) for fluid connection with an outlet or inlet passage (60) for the fluid; and further in that said valve is provided with inlet means for delivering fluid to said orifice in a direction toward said packing, and outlet means for discharging fluid from said orifice, said outlet means discharging said fluid in a direction away from said packing, said inlet means and said outlet means being positioned on the same side of said packing.

19. A manually controlled rod-shaped handpiece having an elongated rod-shaped handle portion, inlet means for receiving energy, outlet means for delivering energy, and actuatable means mounted in said handle portion and adapted to control the transmission of energy from said inlet means to said outlet means, the handpiece further comprising: at least one actuating member mounted in said handle portion and associating with and controlling the operation of said actuatable means, said actuating member adapted to move between a first repose position in which its axis is substantially parallel to that of said handle portion, and a second actuating position in which its axis is displaced relative to that of said handle portion; biasing means for biasing said at least one actuating member into it first repose position; wherein said actuatable means includes a fluid valve comprising a valve housing (48); a valve body (34) supporting a valve packing (36) and having an integral valve rod (26); a valve seat (40) having an orifice (58) normally closed by the packing (36) of the valve body (34); a valve spring (42) for forcing the valve body (34) against the valve seat (40) and for maintaining the normally closed position; and an abutment shoulder in the region of valve seat (40); wherein the valve body (34) and the valve rod (26) are mounted to tilt about an arbitrarily directed tilting axis situated in a plane perpendicular to the axis of the valve rod (26) in its normal position, whereby, when tilting the valve body (34), the same abuts said shoulder at a point of said tilting axis and opens said orifice (58) for fluid connection with said inlet or outlet means; and wherein said actuating member, when in said second actuating position, tilts said valve body (34) and said valve rod (26).

* * * * *